(12) United States Patent
Franks et al.

(10) Patent No.: US 6,751,630 B1
(45) Date of Patent: Jun. 15, 2004

(54) INTEGRATED MULTIPLE BIOMEDICAL INFORMATION SOURCES

(75) Inventors: Dorothy B. Franks, Brentwood, TN (US); Michael C. Jones, Nashville, TN (US); John G. Jaeger, Flower Mound, TX (US)

(73) Assignee: GE Medical Technology Services, Inc., Pewaukee, WI (US)

( * ) Notice: Subject to any disclaimer, the term of this patent is extended or adjusted under 35 U.S.C. 154(b) by 430 days.

(21) Appl. No.: 09/620,028

(22) Filed: Jul. 20, 2000

(51) Int. Cl.⁷ .................................................. G06F 7/00
(52) U.S. Cl. ..................................... 707/102; 707/104.1
(58) Field of Search ............................... 707/100, 104.1, 707/102; 705/2, 28

(56) References Cited

U.S. PATENT DOCUMENTS

| | | | | |
|---|---|---|---|---|
| 4,737,910 A | * | 4/1988 | Kimbrow ........................ | 705/2 |
| 4,937,743 A | * | 6/1990 | Rassman et al. ................ | 705/8 |
| 5,065,315 A | * | 11/1991 | Garcia ............................ | 705/2 |
| 5,400,267 A | * | 3/1995 | Denen et al. ................... | 702/59 |
| 5,557,514 A | * | 9/1996 | Seare et al. ..................... | 705/2 |
| 5,732,401 A | * | 3/1998 | Conway ........................ | 705/2 |
| 5,748,907 A | * | 5/1998 | Crane ............................. | 705/2 |
| 5,778,345 A | * | 7/1998 | McCartney ..................... | 705/2 |
| 5,790,409 A | * | 8/1998 | Fedor et al. ................... | 700/232 |
| 5,799,286 A | * | 8/1998 | Morgan et al. ................. | 705/8 |
| 5,822,544 A | * | 10/1998 | Chaco et al. ................... | 705/2 |
| 5,826,239 A | * | 10/1998 | Du et al. ....................... | 705/1 |
| 5,842,173 A | * | 11/1998 | Strum et al. .................... | 705/1 |
| 5,991,728 A | * | 11/1999 | DeBusk et al. ................. | 705/2 |
| 5,995,937 A | * | 11/1999 | DeBusk et al. ................. | 705/2 |
| 6,076,859 A | * | 6/2000 | Hall et al. ..................... | 283/89 |
| 6,117,073 A | * | 9/2000 | Jones et al. .................... | 705/2 |
| 6,154,728 A | * | 11/2000 | Sattar et al. ................... | 705/28 |
| 6,223,137 B1 | * | 4/2001 | McCay et al. ................. | 705/2 |
| 6,314,556 B1 | * | 11/2001 | DeBusk et al. ................. | 705/2 |
| 6,430,536 B2 | * | 8/2002 | Irving et al. .................... | 705/2 |

OTHER PUBLICATIONS

WO 98/38588– Mayon–White et al. Businsess Analysis Tool and Method. Sep. 3, 1998.*

* cited by examiner

Primary Examiner—Kim Vu
Assistant Examiner—Monplaisir Hamilton

(57) ABSTRACT

Biomedical equipment data records for a medical institution are stored in a database and integrated with other information sources within and external to the institution. The equipment data may include identification of equipment components, departmental assignments, site locations, performance data, service data, and so forth. Additional information resources may include hospital information systems, departmental information systems, financial records, external reference materials, and reference data for similarly profiled institutions. The additional resources provide a basis for more detailed analysis, planning, and reporting of equipment inventory management, performance, and servicing.

29 Claims, 20 Drawing Sheets

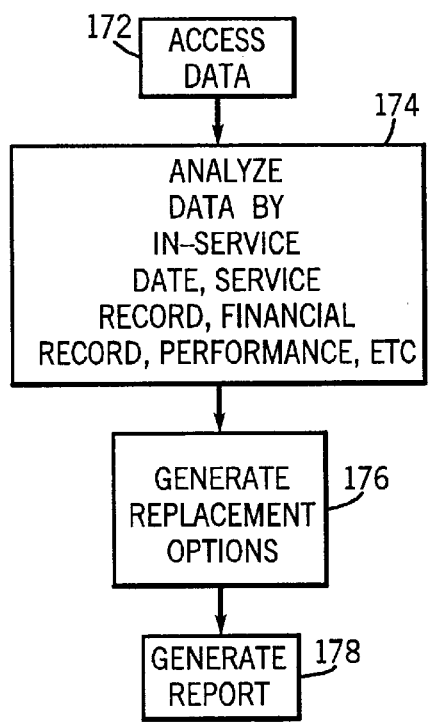
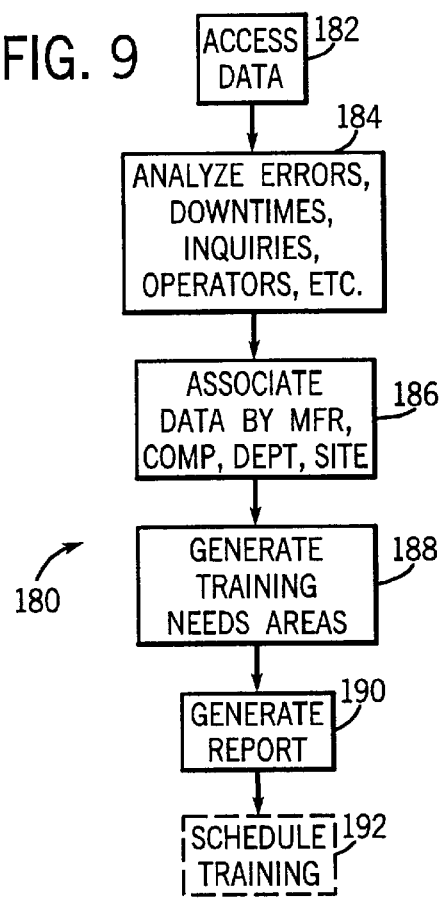
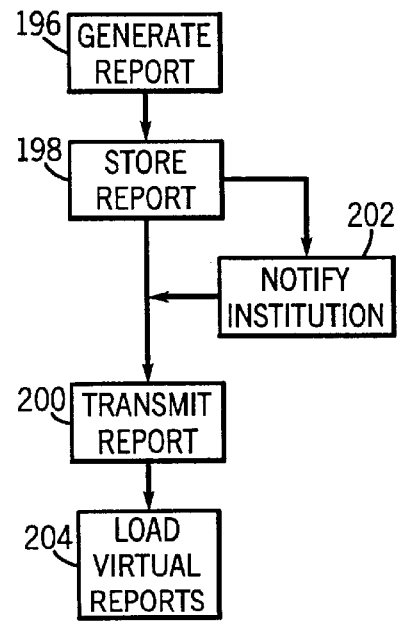

FIG. 13

FAILURE CATEGORY BENCHMARK SUMMARY TABLE (ALL FAILURES)

| FAILURE CATEGORY STATUS | STATUS | FAILURES UNDER CONTRACT | REFERENCE RANGE | REASON FOR NO STATUS |
|---|---|---|---|---|
| OTHER | ☐ | 903 | .0001 TO .0005 | |
| COMPUTER | ☐ | 144 | −.0003 TO .0004 | |
| ELECTRICAL | ☐ | 779 | .0003 TO .0011 | |
| UNKNOWN | ☐ | 9 | −.0002 TO .0002 | |
| MECHANICAL | ☐ | 1305 | .0002 TO .0009 | |
| OPERATOR | ☐ | 160 | −.0003 TO .0004 | |

☐ WITHIN REFERENCE RANGE  ☐ OUTLIERS
☐ OUTSIDE REFERENCE RANGE  ☐ INSUFFICIENT DATA

FIG. 17

EQUIPMENT COUNT BENCHMARK

| EQUIPMENT BY SUB-MODALITY (270) | STATUS (272) | ACTUAL COUNT (274) | REFERENCE RANGE (276) | REASON FOR NO STATUS (278) |
|---|---|---|---|---|
| SUB 1 | ☐ | 34 | 6 TO 21 | REASON 1 |
| SUB 2 | ☐ | 1 | 28 TO 80 | REASON 2 |
| . | ☐ | 5 | 25 TO 131 | . |
| . | ☐ | 7 | 8 TO 23 | . |
| . | ☐ | 25 | 4 TO 22 | . |
|  | ☐ | 26 | 12 TO 24 |  |
|  | ☐ | 8 | 2 TO 7 |  |
|  | ☐ | 11 | 9 TO 42 |  |
|  | ☐ | 265 | 114 TO 272 |  |
|  | ☐ | 90 | 22 TO 97 |  |
|  | ☐ | 57 | 13 TO 63 |  |
|  | ☐ | 19 | 3 TO 21 |  |
|  | ☐ | 148 | 63 TO 165 |  |
|  | ☐ | 2 | 1 TO 4 |  |
|  | ☐ | 383 | 230 TO 915 |  |
|  | ☐ | 2 | 0 TO 6 |  |

REPORTS CONTINUES ON NEXT PAGE

☐ WITHIN REFERENCE RANGE    ☐ OUTLIERS
☐ OUTSIDE REFERENCE RANGE   ☐ INSUFFICIENT DATA

SERVICE COVERAGE REPORT
EQUIPMENT WARRANTY BY FULL SERVICE

| DEPARTMENT | LOCATION | GROUP | EQUIP TYPE | MANUFACTURER | MANUAL | MODEL # | ACQ. DATE | CONTROL # | SERIAL # | SERVICE PROVIDER | EXP / RENEWAL DATE |
|---|---|---|---|---|---|---|---|---|---|---|---|
| DEPT 1 | LOCATION 1 | | TYPE 1 | | | # | 3/1/98 | # | # | | |
| DEPT 2 | LOCATION 2 | | TYPE 2 | | | # | 6/1/99 | # | # | | |
| . | . | | . | | | . | N/A | . | . | | |
| . | . | | . | | | . | N/A | . | . | | |
| . | . | | . | | | . | N/A | . | . | | |
| | | | | | | | N/A | | | | |
| | | | | | | | N/A | | | | |

| MANUFACTURER | EQUIPMENT | # OF BKDWNS | BKDWNS PER YR. | CONTROL # | SERIAL # | AGE/TIME SERVICE | MTTR* (DAYS) | MTBF** (MONTHS) |
|---|---|---|---|---|---|---|---|---|
| | | | | | | | | |
| | | | | | | | | |
| | | | | | | | | |
| | | | | | | | | |
| | | | | | | | | |
| | | | | | | | | |
| | | | | | | | | |

BREAKDOWN DETAILS BY DEPARTMENT  *MEAN TIME TO REPAIR
DEPARTMENT 1  **MEAN TIME BETWEEN FAILURES

FIG. 22

HOSPITAL − INSTITUTION 1

| DEPARTMENT | BREAKDOWN COUNT |
|---|---|
| DEPT 1 | 79 |
| DEPT 2 | 140 |
| . | 24 |
| . | 3 |
| . | 131 |
|  | 59 |
|  | 1 |
|  | 24 |

REPORTS CONTINUE ON NEXT PAGE...
↑ ↑
330 332

SUGGESTED INVENTORY ENHANCEMENT SUMMARY
(5 YEAR FORECAST)
INSTITUTION 1

SUGGESTED INVENTORY REPLACEMENT SUMMARY
BASED ON INDUSTRY DATA – CONTINUED

| EQUIPMENT SUB-MODALITY | CURRENT COUNT | 2004 FORECAST NEED | POTENTIAL RETIREMENTS BETWEEN NOW AND 2004 | NET ADDITIONAL NEED |
|---|---|---|---|---|
| SUB 1 | 12 | 13 | 8 | 9 |
| SUB 2 | 1 | 1 | 1 | 1 |
| . | 10 | 11 | 7 | 8 |
| . | 4 | 4 | 4 | 4 |
| . | 2 | 2 | 2 | 2 |
|  | 1 | 1 | 1 | 1 |
|  | 12 | 13 | 9 | 10 |
|  | 12 | 13 | 9 | 10 |

REPORTS CONTINUE ON NEXT PAGE...

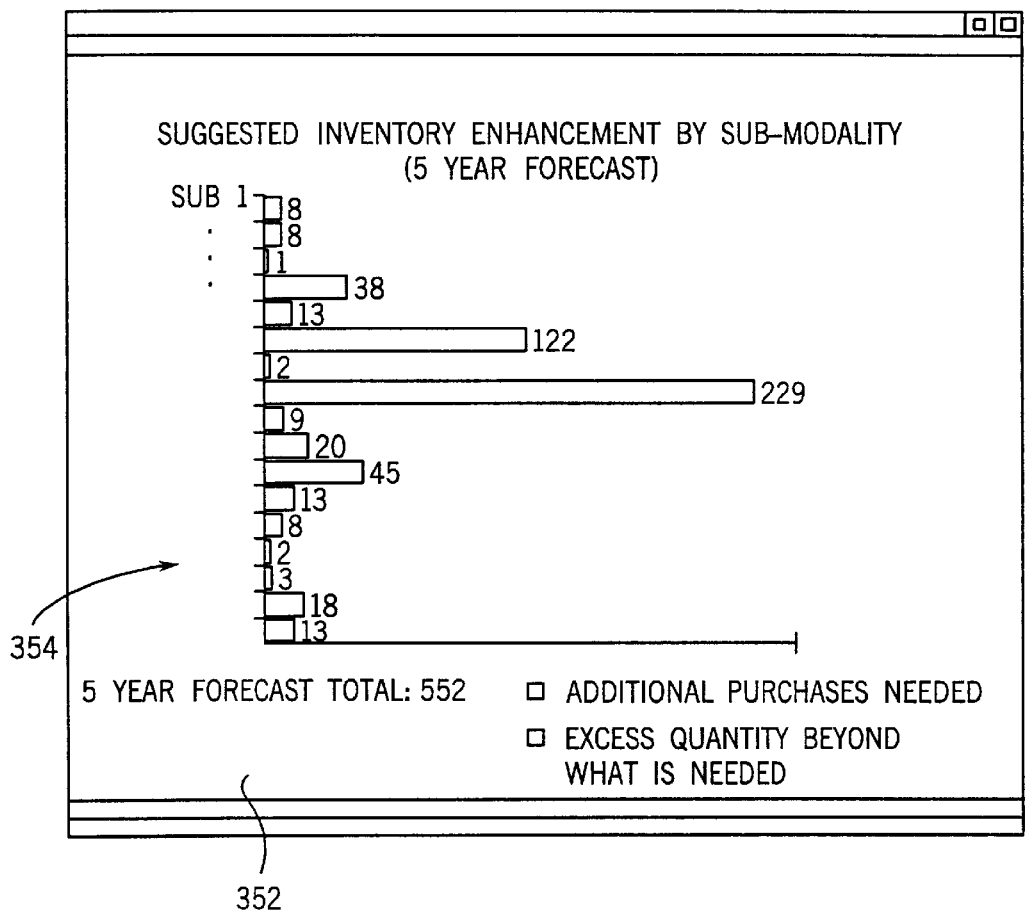

INTEGRATED MULTIPLE BIOMEDICAL INFORMATION SOURCES

FIELD OF THE INVENTION

The present invention relates generally to the field of medical systems, equipment, institutions, and so forth. More particularly, the invention relates to a technique for integrating information sources for medical equipment and facilities so as to permit enhanced data analysis and reporting within, between, and among facilities.

BACKGROUND OF THE INVENTION

Modem medical diagnostic facilities draw upon a wide range of resources to provide high-quality medical care. Such resources include the physical plant needed to accommodate patients and medical care staff, disposable and non-disposable equipment and resources utilized in providing medical care, and human resources critical in providing the care. Proper management of such facilities, which is subject to the same business constraints as any other highly technical business operation, requires detailed analysis of asset utilization for financial allocation and planning.

Current techniques for managing data in medical facilities includes manual and automated collection of data from individual areas, departments, and systems. In a typical institution, assets utilized for patient care are tracked for billing purposes, such as by input into a hospital information system (HIS). Maintenance of more technical resources, such as imaging and monitoring systems, is typically separate from the HIS, and may include records kept by hospital personnel, as well as by on or off-site contractors maintained to support the equipment. Similarly, support personnel employed to maintain the physical plant, including a wide range of equipment and components from lights to building systems, to grounds maintenance, often keep entirely separate records. Moreover, the individual records kept for asset and resource utilization and medical institutions is generally not associated with similar records derived from known populations, or even financial information for the same or similar equipment to permit more detailed asset management.

There is a need in the field of medical equipment and facilities for an improved technique for integrating various information sources to permit enhanced data analysis and reporting. At present, information resources are often separated both within institutions, and between institutions, even where the institutions are logically associated in a single or related business. Similarly, present techniques do not typically associate centralized records for an institution or medical business with similar data for the purposes of benchmarking, financial analysis or financial tracking. There is a need, therefore, for an integrated system which permits such comparison and analysis on a secure and rapid basis.

SUMMARY OF THE INVENTION

The present technique offers integration of multiple resources of information and data within and between medical institutions designed to respond to these needs. The system may incorporate conventional data collection and input processes, including manual input by individual service providers and departments. The information collected may also originate through automated collection techniques, such as through remote monitoring of individual systems or departments. The data is associated with the source to permit a detailed analysis, but is also associated with the overall department, institution, or business to allow for higher-level analysis. The integrated system also includes data not normally available from individual institutions, including financial planning data, and population data that allow for financial tracking and planning, and benchmarking against institutions or equipment with similar profiles or missions.

The technique further offers for rapid and accurate reporting of analysis based upon the collected data and upon the input from the extraneous sources, including the financial and benchmarking sources. Reports may be generated in a secure fashion and delivered to institution management personnel such as through secure network links. Where information is collected for benchmarking purposes, the information may be filtered to avoid identification of particular institutions or data sources where desired. The resulting reports provide an accurate and highly detailed view of asset utilization for both institutions and subdivisions within institutions. Moreover, the reports may provide detailed analysis of trends, including in both physical plant and equipment utilization, and in human resource needs.

BRIEF DESCRIPTION OF THE DRAWINGS

FIG. 8 is a flow chart illustrating exemplary control logic for equipment replacement and planning processing;

FIG. 9 is a flow chart illustrating exemplary control logic for analysis of data to determine possible areas for staff training;

FIG. 10 is a flow chart illustrating exemplary control logic for report delivery based upon analysis summarizing the foregoing figures;

FIGS. 12–25 are exemplary report screens illustrating report analysis for biomedical equipment presenting data for departments, groups, sites, and individual equipment components and types in accordance with aspects of the present technique.

DETAILED DESCRIPTION OF THE INVENTION

Figure 1:
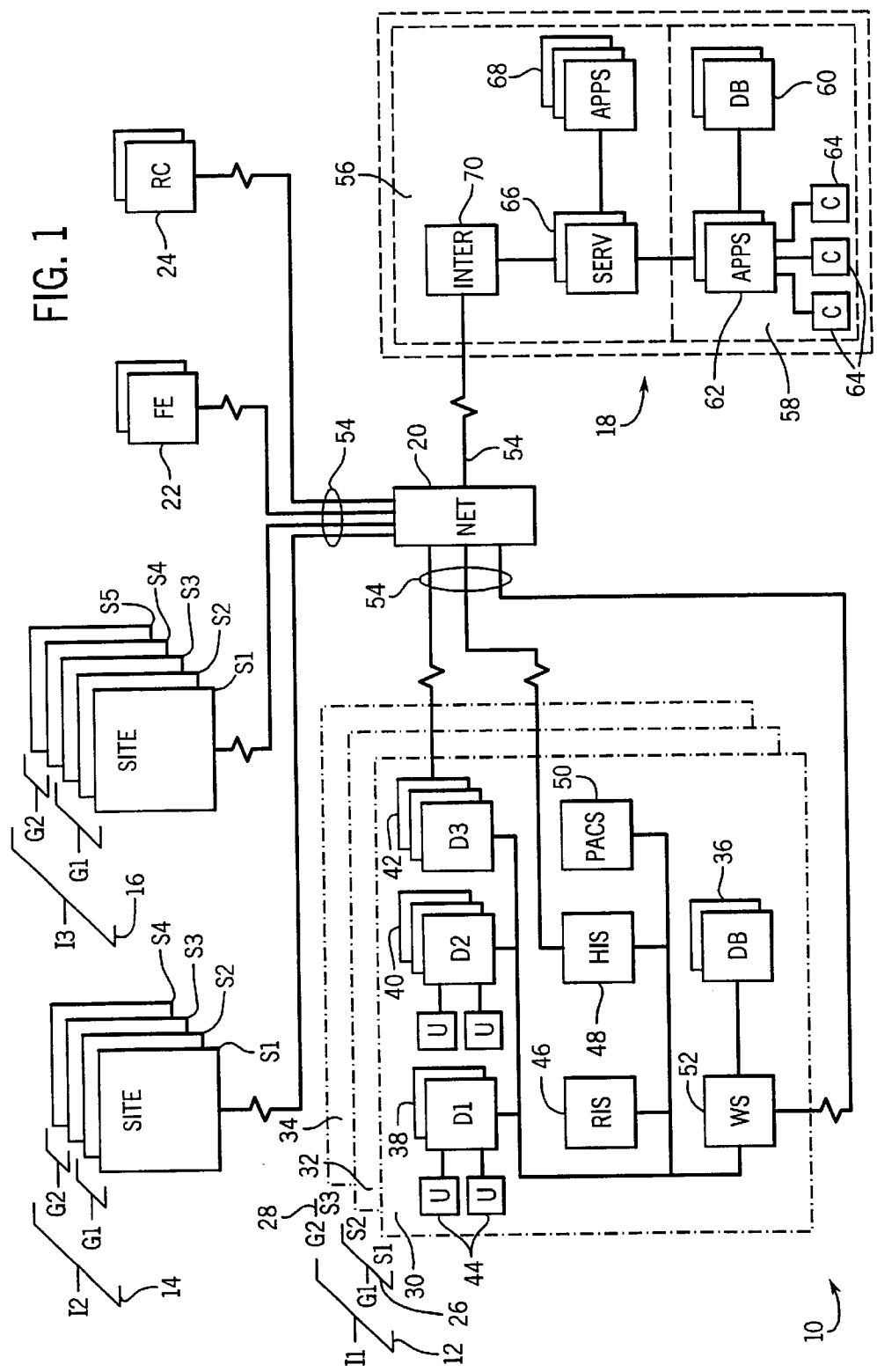
FIG. 1 is a diagrammatical representation of a service system for collecting and analyzing data in one or more medical institutions.

Turning up to the drawings, and referring first to FIG. 1, a service system 10 is represented for monitoring, data collection, data analysis, and reporting relating to biomedical equipment in one or more medical institutions. As illustrated, system 10 includes a plurality of institutions 12, 14 and 16, details of which are represented only for the first institution 12. In accordance with aspects of the present technique, any number of institutions may be serviced by a topography such as that illustrated in FIG. 1, or various modified topographies employing the techniques described below. System 10 further includes at least one service provider 18 which services the biomedical equipment of the institutions, collects and analyzes data on the equipment, and provides reports relating to the equipment inventory, performance, and so forth. In the illustrated embodiment, the institutions and the service provider may be linked via a network 20, such as the Internet. In a general implementation, the system may also permit access of data records by field engineers or technicians 22, and by remote clients 24. The field engineers and remote clients may, where appropriate, access or input data via mobile computer systems, remote computer terminals, and so forth.

Within each institution, a variety of functional portions or subdivisions may be defined, and data collected and analyzed in accordance with such functional portions. In the embodiment of FIG. 1, for example, institution 12 includes two functional groups 26 and 28, and three facility sites 30, 32 and 34. Sites 30 and 32 comprise group 26, while site 34 forms group 28. As will be described below, the present technique facilitates a collection and centralized storage of biomedical equipment data for individual sites, individual departments within the sites, institutions, and logical groupings. By way of example, where an institution includes sites in geographically dispersed locations, each site may be accounted for separately, but with the equipment data being referenced by site and institution, permitting an overview by either the site or the institution. Similarly, logical groupings, such as by political subdivisions (e.g., state, country, city) or fiscal or taxing jurisdictions may be specified and the data accordingly referenced.

Within each site, a variety of departments and systems may be designated and interfaced with one another. A centralized database 36 is compiled including data relating to biomedical equipment maintained (e.g., owned, managed, leased) by the institution. It should be noted that the database could be stored on any suitable memory device, and multiple memory devices, as shown, may be provided for storage of all or part of the database, or to provide backup and redundancy in storage. In general, however, the centralized database forms, for the user, a central repository for biomedical equipment data which can be accessed, processed, transferred, stored, and maintained to facilitate the tracking, management, planning, and other decision-making.

In the embodiment of FIG. 1, institution 12, at site 30, includes a variety of departments 38, 40 and 42. Depending upon the mission of the institution, these departments may include radiology departments, emergency care facilities, neonatal care facilities, oncology units, and so forth. Within each department, biomedical equipment will be maintained for providing medical care to in-patients and out-patients. In the present context, the biomedical equipment may include a wide range of disposable and non-disposable resources, such as patient monitors, input and readout devices, and so on. Generally, however, the biomedical equipment may also include elements of the physical plant of the institution, including beds, wheelchairs, computer systems, and so forth. In certain departments the equipment may further include imaging stations, scanners, probes, coil assemblies, and so forth. The equipment of each department is available for operation by nurses, clinicians, physicians, and other users, as indicated diagrammatically by reference numeral 44 in FIG. 1.

In addition to the biomedical equipment assigned to each department, the institution may include additional systems which are interfaced in the institution information system. For example, a radiology department information system (RIS) 46, a hospital information system (HIS) 48, a picture archiving and communication system (PACS) 50, and a similar information management systems may be provided. One or more management stations 52, such as a conventional computer workstation, is provided, preferably at each site, for reviewing reports and data generated as described below. It should be noted that a variety of such management stations may be provided, including fully or partially enabled management stations within each department. Various departments and systems within the institution will be provided with configurable network interfaces, such as modems or other network connections, so as to facilitate transmission and reception of data via network links 54 and network 20.

Service provider 18, which may function partially within the institution itself, includes processing capabilities for accessing, analyzing and reporting on data collected by the institutions on the biomedical equipment. It should be noted, however, that in the embodiment illustrated in FIG. 1, the service provider 18 may maintain facilities remote from one or more of the institutions and one or more of the facility sites, with data being transmitted between the institutions and the service providers via network 20. In the embodiment illustrated in FIG. 1, service provider 18 includes processing capabilities divided into a first processing space 56 and a second processing space 58. As described below, to maintain heightened security for data stored by the service provider, processing space 58 may be separated from space 56 to substantially limit access to processing space 58 from users outside the service provider system. In the present context, space 58 serves to store biomedical equipment records, to process data from the records, and exports data files for generation of reports within processing space 56. Thus, one or more databases 60 are maintained by the service provider 18, with processing capabilities in a form of specific applications 62 provided for storing, associating, analyzing, and extracting data from the database. Clients 64 may access the applications for performing the data manipulation functions at the service provider. One or more servers 66 are linked to the applications 62 to receive data files used as the basis for generating equipment reports. Additional applications 68 serve to format and process the reports. Finally, a network interface 70 is provided, such as including a router, modems, or similar network interface circuitry, for receiving data and transmitting data and reports to the medical institutions from the service provider.

Figure 2:
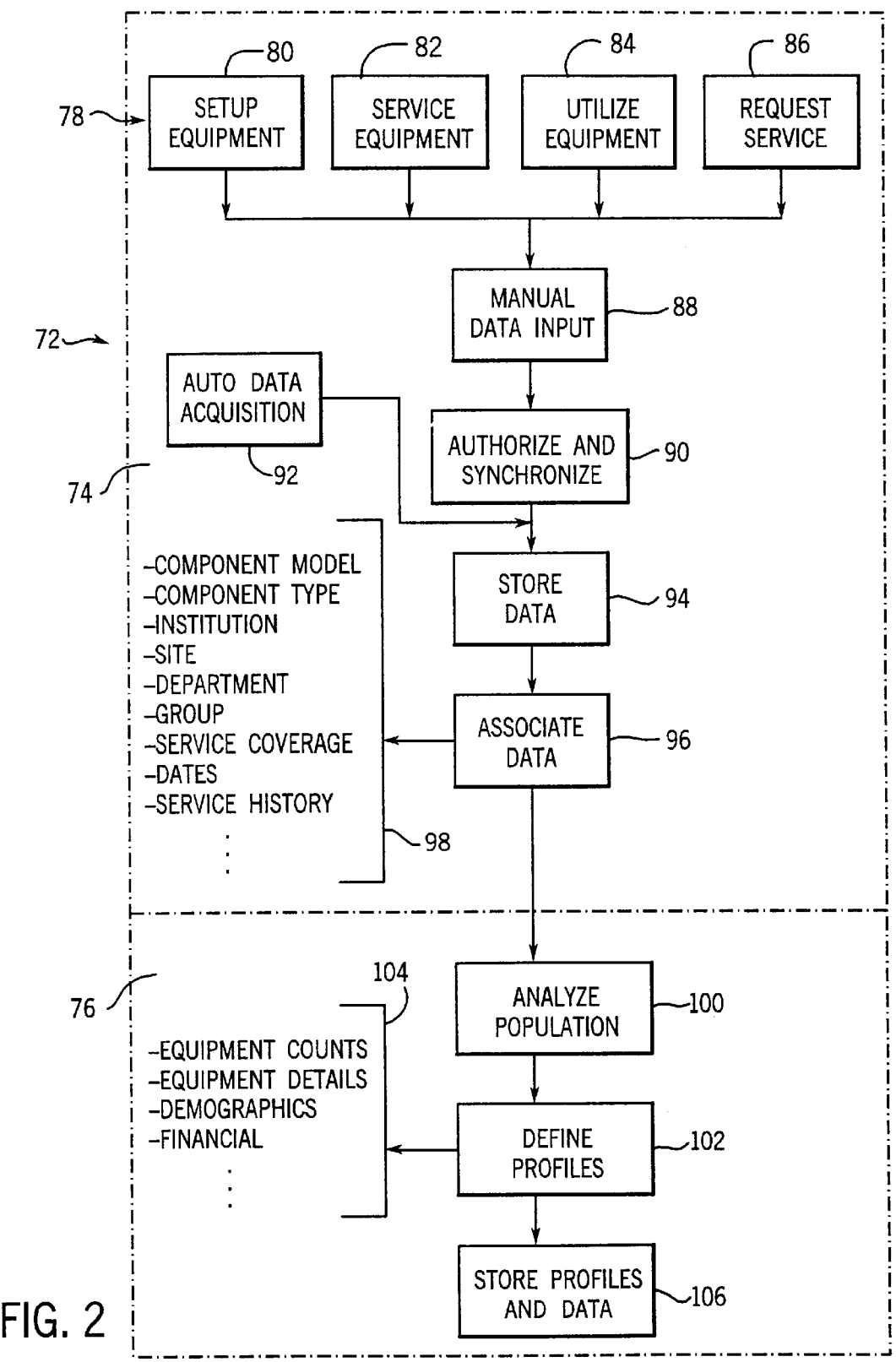
FIG. 2 is a flow chart representing exemplary control logic for collecting and analyzing the data system of the type illustrated in FIG. 1.

FIG. 2 represents exemplary logic for accessing or collecting, storing, and analyzing biomedical equipment data in a system of the type illustrated in FIG. 1. The processing illustrated in FIG. 2 may be logically subdivided into a data collection/storage/association sequence 74, and a population data analysis sequence 76. Within the sequence 74, data is collected for biomedical equipment within departments, sites, groups and institutions either manually, as indicated at reference numeral 78, or by automatic acquisition. Any suitable data input technique may be employed, typically including manual input via a workstation, laptop computer, handheld device, and so forth. Thus, as illustrated in FIG. 2, input may be by equipment setup upon its initialization, as indicated at reference numeral 80, or by subsequent servicing (i.e., as individual equipment components are serviced) as indicated at reference numeral 82. Other data may be manually input as the equipment components are utilized as indicated at 84, or upon specific service requests as indicated at reference numeral 86. At any one of these or other points in the operation of the biomedical equipment, the data relating to the equipment is thus manually input as indicated at reference numeral 88. To limit access to the data input system, and to maintain the integrity of the data, an authorization and synchronization sequence 90 is preferably implemented, such as through password protection, permitting authorized personnel only or authorized stations to input equipment data. Synchronization is performed to maintain up-to-date equipment data once the input is performed.

As an alternative to manual data input, certain automatic data acquisition may be performed as indicated at reference numeral 92 in FIG. 2. Automatic data acquisition may include polling of certain equipment, such as at regular intervals or according to a regular schedule. Networked equipment may thus be tracked and its performance monitored through data stored at the equipment and transmitted at step 92. Following either step 90 or 92, the data is stored as indicated at reference numeral 94. As noted above, the data may be stored at one or more storage devices, but with the data being associated in a centralized database for the institution. Again, the centralized database may be located physically at one or more of the institution sites, or off-site, such as at a location of the service provider 18.

At step 96, the data collected for the biomedical equipment is associated in the centralized database in accordance with any number of logical references. The data itself preferably includes references which facilitate or comprise the association as indicated at reference numeral 98. Thus, the component data may include both the identification of the component, the component model, including its manufacturer and model designation, and a component type, typically indicated by the function of the equipment. The data also preferably includes a reference representative of the institution, the site at which the components are located, the departments to which the components are assigned, if assigned, and the group designation for associating the departments or sites logically. The service data for each component also preferably includes a reference to service agreements or contracts for all or partial coverage of the components, including original warranty data and after-purchase service contracts or subscriptions. Relevant dates are preferably included, such as the date of purchase or entry into service, dates of servicing, and expiration or renewal dates for service arrangement coverage. Moreover, specific service history information may be included, where individual components have been regularly serviced or serviced on an as-needed basis. Such service history data may also include error codes, service request records input by the institution or users, breakdown records, downtime records, subcomponent replacement records, and so forth.

The population data analysis sequence 76 permits benchmarking or profiling of specific institutions and groups of institutions in accordance with equipment usage characteristics and other considerations. Where the service provider has access to equipment records for a range of institutions, the records are preferably analyzed to identify commonalities between the institutions, sites, departments, and groups. Such analysis may include consideration of the types of institutions, the types of departments, the types of equipment utilized, and the utilization characteristics (e.g., number of components, duty imposed on components, replacement or service records, and so forth). Based upon the analysis, characteristic profiles are identified which correspond to typical institutions, sites, departments, or groups that may be used as a basis for comparing a particular institution by equipment inventory and utilization for benchmarking purposes. It should be noted that benchmarking analysis preferably results in profiles which do not identify any individual institution, but which identify only a larger groups of institutions (such as groups of 20 or more) considered representative of a particular profile. The profiles, defined at step 102, may thus include reference data 104 such as equipment counts, equipment details, demographics, and financial profiles. At step 106 the profiles and corresponding reference data are stored, preferably in the database for the service provider, for future reference in benchmarking and service planning as described below.

Figure 3:
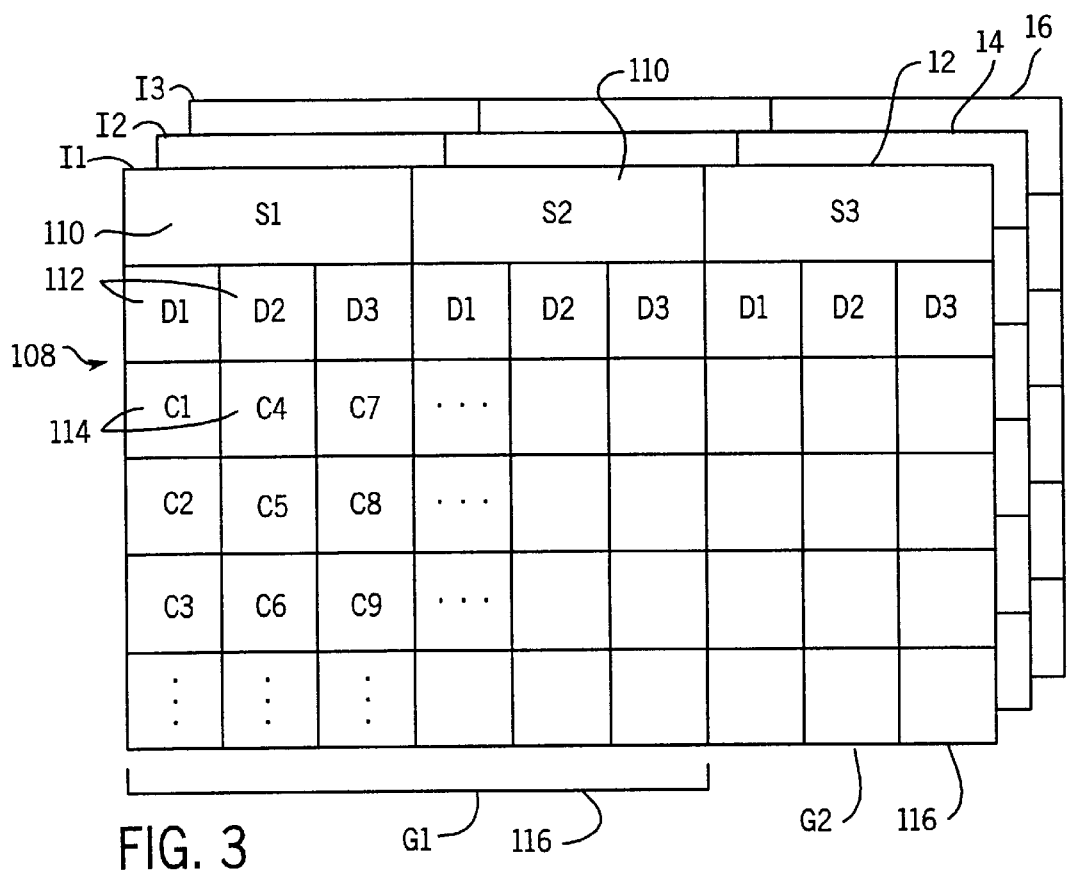
FIG. 3 is a diagrammatical representation of data records including data associated with institutions, sites, departments, groups, and components collected and processed in accordance with the aspects of present techniques.

The biomedical equipment records stored in the centralized database thus form a dataset or structure which permits and facilitates analysis by institution, site, department, group, component, component type, and other reference features. The database records may be considered to form a multi-dimensional data matrix structure which inter-relates these various aspects of the equipment component data as illustrated in FIG. 3. As shown in FIG. 3, the data record 108 for an institution 12 may thus include references 110 to specific facility sites at which equipment components are located. Additional departmental records 112 specify the department to which equipment components are assigned. Records for each department and site are then maintained for each component at reference numeral 114, including the identification and service information of the type described above. Moreover, the site, department, and component records may be associated by group designations 116. Where additional institutional records are available to the service provider, these may form a similar databases as illustrated in FIG. 3, permitting the analysis of groups of institutions to establish the profiles mentioned above.

Figure 4:
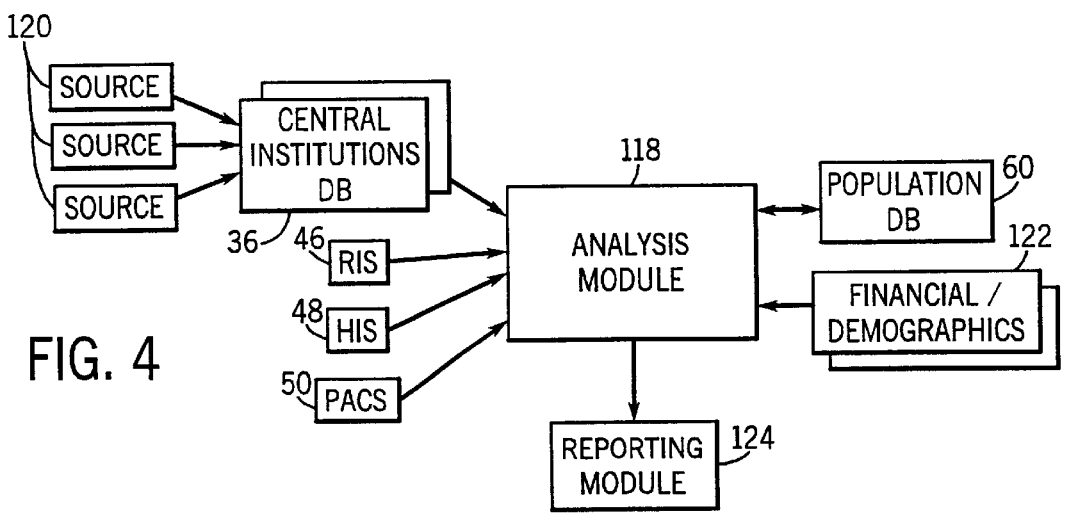
FIG. 4 is a data flow diagram illustrating the multiple sources of data utilized in analysis and reporting of institutional biomedical equipment data.

It should be noted that the present technique provides not only a centralized database for maintaining medical institution equipment records, but integrates a wide range of informational sources both at the institution and sources available to a service provider. FIG. 4 illustrates diagrammatically an example of the types of information sources which are integrated through the present technique. As described below, an analysis module 118 is provided either at the institution, or preferably at the service provider for accessing and analyzing the equipment records. The analysis module may incorporate a range of analysis algorithms, search techniques, and software applications, for deriving useful management data from the component records. In a general sense, the analysis module performs counts, statistical analysis, and associations of the equipment components by site, department, institution, group and manufacturer, as well as by any other references provided in the component records. The analysis module draws such information from the institutional database 36, as well as from other information systems of the institution, such as the RIS 46, the HIS 48, any PACS 50 present in the institution, or other institutional information systems. Again, the central institution database 36 may, in turn, obtain information from various sources, designated generally by reference numeral 120 in FIG. 4, such as departmental data entry systems, stationary or mobile data input devices, field engineer or service personnel laptops, and so forth. Similarly, analysis module 118 accesses information from population databases 60, such as for comparison in benchmarking, as well as financial, demographics, and other input 122, which may include publicly available sources, such as searchable databases, industry-specific databases, and so forth. Based upon analysis performed by the analysis module 118, a reporting module 124 is provided for generating and delivering reports representative the component records, and analysis derived from the component records.

Figure 5:
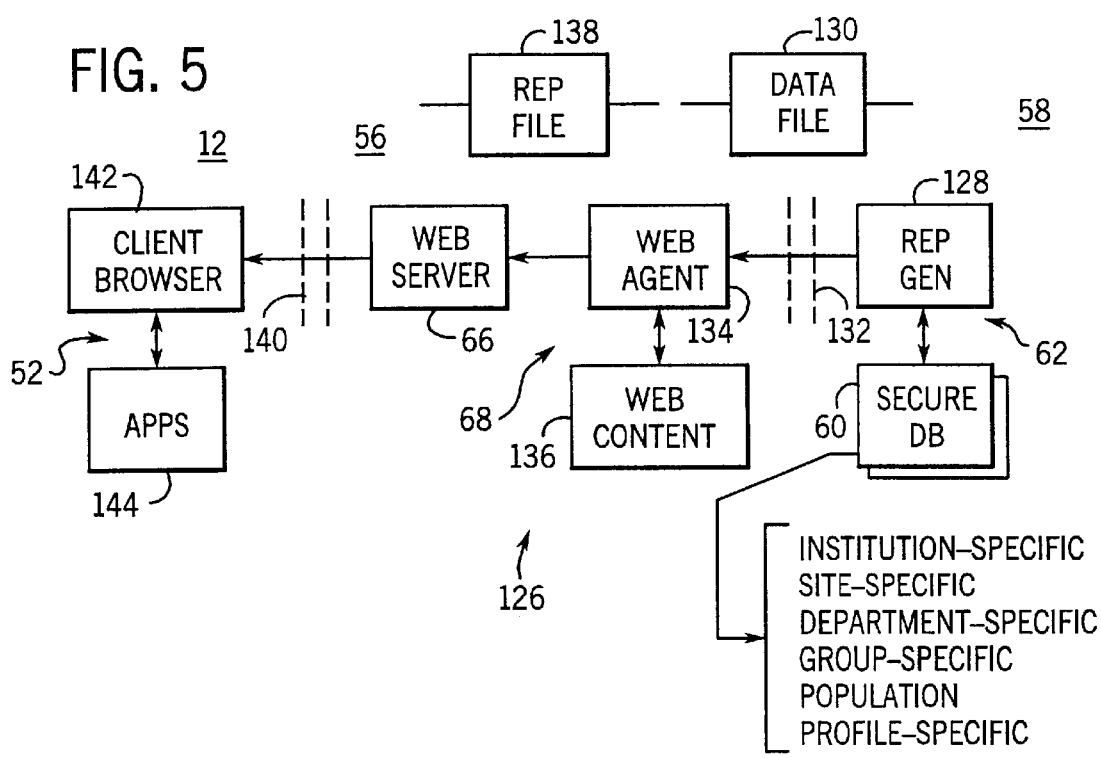
FIG. 5 is a work flow diagram illustrating functional components for securely generating reports based upon collected equipment data and for delivering the reports to a medical institution.

FIG. 5 is a diagrammatical representation of reporting workflow, designated generally by reference numeral 126, for operation of the analysis and reporting modules of FIG. 4. As shown in FIG. 5, the service provider secure database 60 is maintained in the secure processing space 58. Among the software applications 62 operative in the secure processing space 58, is a report generation application 128, which forms part of the reporting module represented generally at reference numeral 124 in FIG. 4. On a periodic basis, or upon request, the report generation application 128 accesses the data record 108 (see, e.g. FIG. 3) for the institution, and calculates or derives any inter-related data not already contained in the record for use in a management report or reports to be transmitted to the medical institution. In the example illustrated in FIG. 5, the data record includes information which institution-specific, site-specific, department-specific and group-specific. Moreover, database 60 may also include a data representative of known populations of medical institutions, sites, groups, or components, as well as pre-calculated data which is profile-specific. As noted above, the profiles generated based upon known population data may categorize institutions and other logical groupings by size, demographics, and so forth. Report generation application 128 produces a data file 130 containing data or fields of data, which is then exported via a firewall 132 to processing space 56.

Within processing space 56 additional hardware and software components are provided for translating the data file 130 into one or more report files. Thus, in the illustrated embodiment, applications 68 within the processing space 56 include a web agent 134 which is adapted to place data from file 130 into a predefined report template. Other web content, and input for generating the report is provided in one or more files 136. By integrating the data file and web content in the predefined report template, a report file 138 is generated, which may be adapted for presentation in any suitable manner, such as an HTML page on a conventional web browser. The report file 138 is then stored and is available for distribution via a web server 66.

In a present implementation, the web server 66 transmits the report file 138 via a configurable network link, such as the Internet, and through a firewall 140. At the medical institution 12, and typically at a management station 52, a client browser application 142 facilitates viewing and navigating through various portions of the report as described more fully below. Additional applications 144 may be available for manipulation of the report, formatting of the report, printing of hard copies and so forth.

Figure 6:
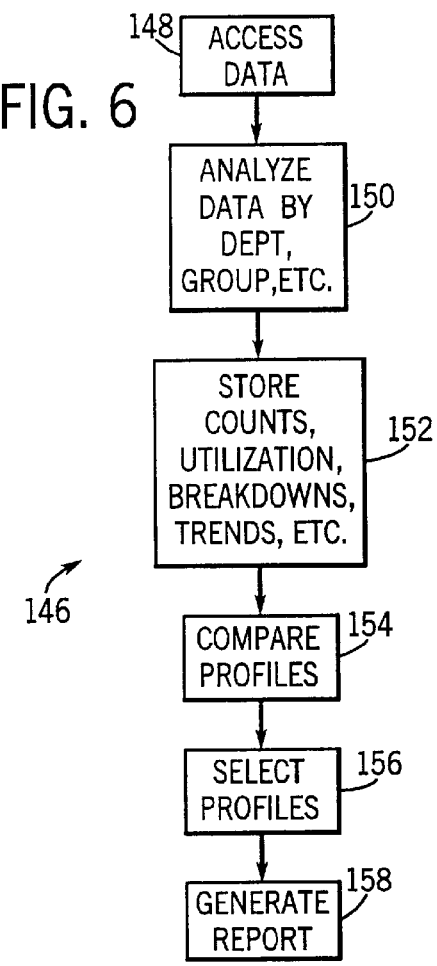
FIG. 6 is a flow chart illustrating exemplary control logic in departmental and group data processing in accordance with aspects of the present techniques.

As noted above, the present technique permits analysis of biomedical equipment data by various functional portions of a medical institution, such as by department or group. The data stored in the centralized database and accessed by the service provider is thus referenced by the functional portions, typically a department to which equipment components are assigned, or a site and group in which the components are located. FIG. 6 illustrates exemplary steps in control logic for processing the data to generate reports of equipment by department, group, site, or other logical division.

As shown in FIG. 6, at step 148, the data is accessed from the centralized database, and at step 150 the data is analyzed by the desired logical subdivision, such as the department or group. In a presently preferred embodiment, data is analyzed to identify the number of each component model and type, as well as to determine utilization parameters (e.g., time utilized or operations performed), breakdowns, error codes, trends, and so forth. Moreover, current data may be analyzed along with historical data stored in the centralized database, or in a historical database, to identify trends in these parameters over time. Thus, the analysis performed at step 150 may identify increases or decreases in the numbers of equipment components, increases or decreases in errors, breakdowns, and so forth. At step 152, the data generated by the analysis of step 150 is stored for later use in generating a report to the medical institution as described above. At step 154, all or some of the data originally collected, or derived from the original data, may be compared to reference data for similar institutions in accordance with predefined profiles as described above. The data itself may serve as the basis for selecting a comparable profile after the comparison of step 154, as indicated at step 156. Based upon the selected profile, benchmarking parameters may be generated which may provide an overview of the equipment inventory, performance, utilization, and servicing of the biomedical equipment of the institution with comparable institutions as defined by the profile. At step 158 a report is generated in accordance with the department, site, and group designation as described above with respect to FIG. 5.

Figure 7:
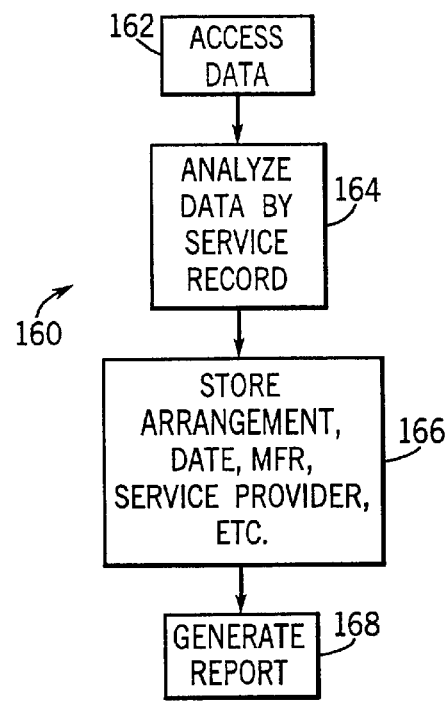
FIG. 7 is a flow chart illustrating exemplary control logic for service arrangement analysis and processing.

The present technique also permits detailed analysis of service arrangement coverage for biomedical equipment. As indicated by the control logic 160 summarized in FIG. 7, processing of the stored data to identify a service arrangement coverage begins at step 162 where the data is accessed. At step 164, the equipment records are analyzed by service record, to identify the equipment identification, its type, any existing warranties, service arrangement and subscriptions, and so forth. It should be noted that this information may include designations by department, site, group, or any other appropriate subdivision of the institution as summarized in FIG. 6. The resulting data summaries are stored at step 166 for generation of a report at step 168.

An additional functionality of the present technique permits the equipment data to be analyzed for scheduling or planning replacement of equipment, expansion in inventory, reductions in inventory, servicing, and so forth. Exemplary logic in the planning processing is summarized in FIG. 8 and designated generally by reference numeral 170. The processing 170 begins with access of the data at step 172, followed by analysis of the data by parameters such as the in-service date, the service record, financial records, performance records, and so forth. For example, specific biomedical equipment components may be scheduled for replacement a predetermined time after they are placed in service, such as in accordance with depreciation schedules, scheduled turnover of equipment, and so forth. Moreover, service records may provide a forecast of anticipated replacement needs for the equipment. Similarly, error codes or breakdown records may serve as the basis for forecasting possible replacement of the components. Where appropriate, anticipated changes in demographic information may also be used in the analysis of step 174, such as to plan for future expansions or reductions in inventory in accordance with anticipated needs of the institution. It should also be noted that, where desired, the replacement and planning processing of FIG. 8 may be performed for specific departments, sites, groups and other functional portions of the institution. At step 176, based upon the analysis of step 174, counts and types of equipment replacement are forecast and stored.

Where desired, these forecasts may include accounting for anticipated costs of replacement, such as based upon current costs of the replacement items. At step 178 a planning report is generated based upon the analysis and replacement options.

A further type of processing which may be facilitated by the present technique is directed to identifying potential training needs based upon utilization of the biomedical equipment components. FIG. 9 represents steps in exemplary control logic for carrying out this processing, as indicated generally by reference numeral 180. The processing begins at step 182 where data for the components is accessed from the centralized database. At step 184, the data is analyzed to identify factors which may be indicative of a need for staff training. By way of example, such factors may include logged errors, downtimes, service or procedural inquiries, and so forth. In addition to identification of the particular components and training-indicative parameters, the data may also be analyzed to identify specific operators or users who may benefit from additional training. At step 186 the data is associated to identify the training needs by factors such as the equipment manufacturer, the component type, the department, the facility site, and so forth. Based upon the analysis made at steps 184 and 186, training needs are identified at step 188, and a report reflecting possible needs is generated at step 190. Again, the report generated at step 190, which may be generated in accordance with FIG. 5, may indicate specific training needs for specific equipment or equipment types, and may identify specific departments, sites, groups, or even specific users which may benefit from the training. As an optional step, actual training may be scheduled as indicated at step 192.

The various analyses and report generation steps described above, carried out generally in the secure manner summarized in FIG. 5, may produce reports which can be transmitted by various means to the management decision-makers of the medical institution. FIG. 10 illustrates a presently preferred manner of transmitting the reports via a configurable network. The process, designated generally by reference numeral 194, begins with generation of the report as indicated at reference numeral 196. At step 198 the report is stored, such as by generation of a data file, and combination of a data file with a report template to produce a report file or files. The report may be transmitted directly to the medical institution electronically, such as via a configurable network connection, as indicated at reference numeral 200. Alternatively, a notification may be sent to the institution, such as through the configurable network, notifying the institution that the report is available for downloading as indicated at step 202. The institution may then pull the report at any convenient time. Once the report is transmitted to the medical institution, it may be loaded and viewed on a management workstation as indicated at step 204. It should be noted, that the foregoing reports may be generated separately or in combination.

Moreover, in a present embodiment, a single report file may include a wide range of "virtual reports" each of which includes details or user viewable pages with specific information relating to components, departments, sites, groups, and so forth.

The reports provided by the present technique may be formatted in any suitable manner. However, in a present embodiment, the reports are generated electronically, and are transmitted to the medical institution via a configurable network connection, such as in the form of HTML pages which can be opened and viewed in a conventional web browser or other display application. FIGS. 11–25 illustrate exemplary pages in such reports generated through logic such as that described above and based upon information collected in centralized database of a medical institution.

Figure 11:
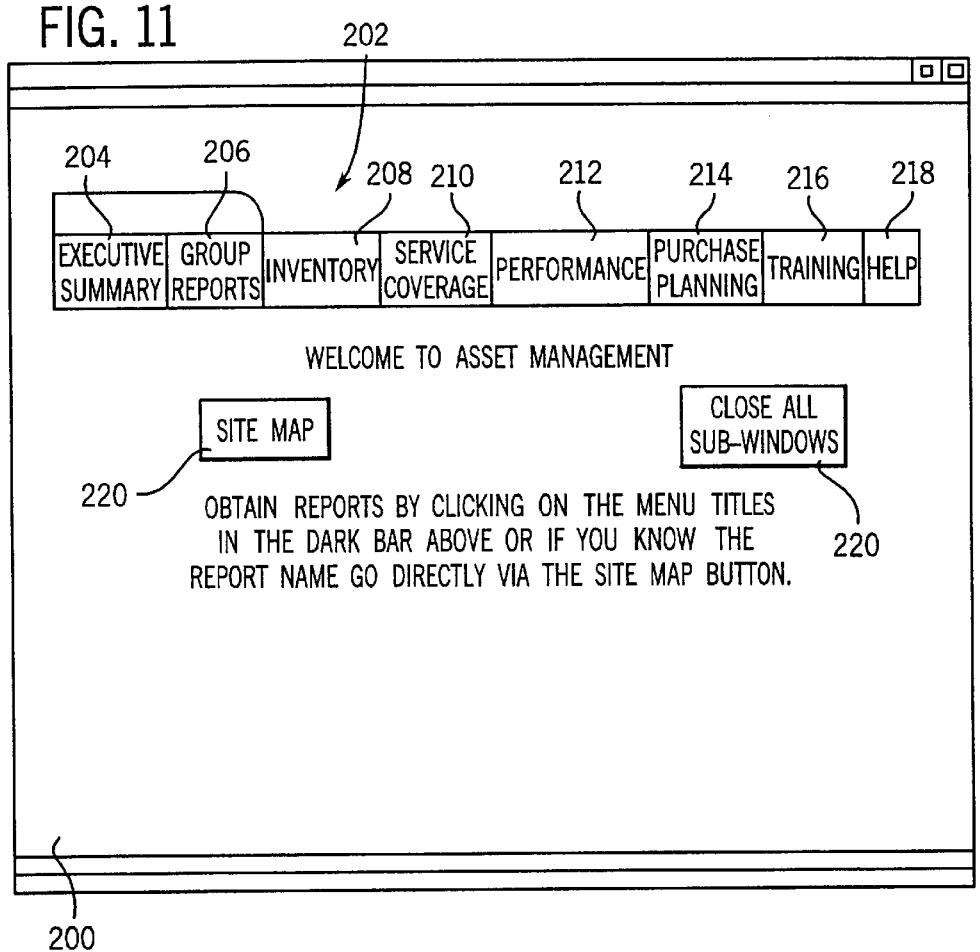
FIG. 11 is an exemplary graphical user interface screen, such as a browser screen, for accessing analyzed data and virtual reports.

FIG. 11 illustrates a summary or navigation page which is accessed in a conventional web browser for viewing additional report pages. As noted above, the report delivered in accordance with the foregoing techniques may include a wide range of data subdivided and associated in a manner so as to present information for individual equipment components, groups, sites, and so forth. In the present embodiment, the page illustrated in FIG. 11, designated generally by the reference numeral 200, provides for navigation through the various "virtual reports." The page preferably includes graphical user interface tabs or buttons 202 which can be selected by user for navigating through the more detailed reports. In the illustrated embodiment, such virtual buttons are provided for an executive summary 204, group reports 206, inventory analysis 208, service coverage analysis 210, performance analysis 212, planning analysis 214, and training analysis 216. Additional tools can be provided, such as a help tool 218, as well as alternative navigational tools 220, permitting the user to directly access virtual reports or to navigate or exit the report. As will be appreciated by those skilled in the art, various additional tools (not represented) can be provided, such as tools for reviewing previous pages, advancing to further pages, printing pages, searching through pages, and so forth.

Figure 12:
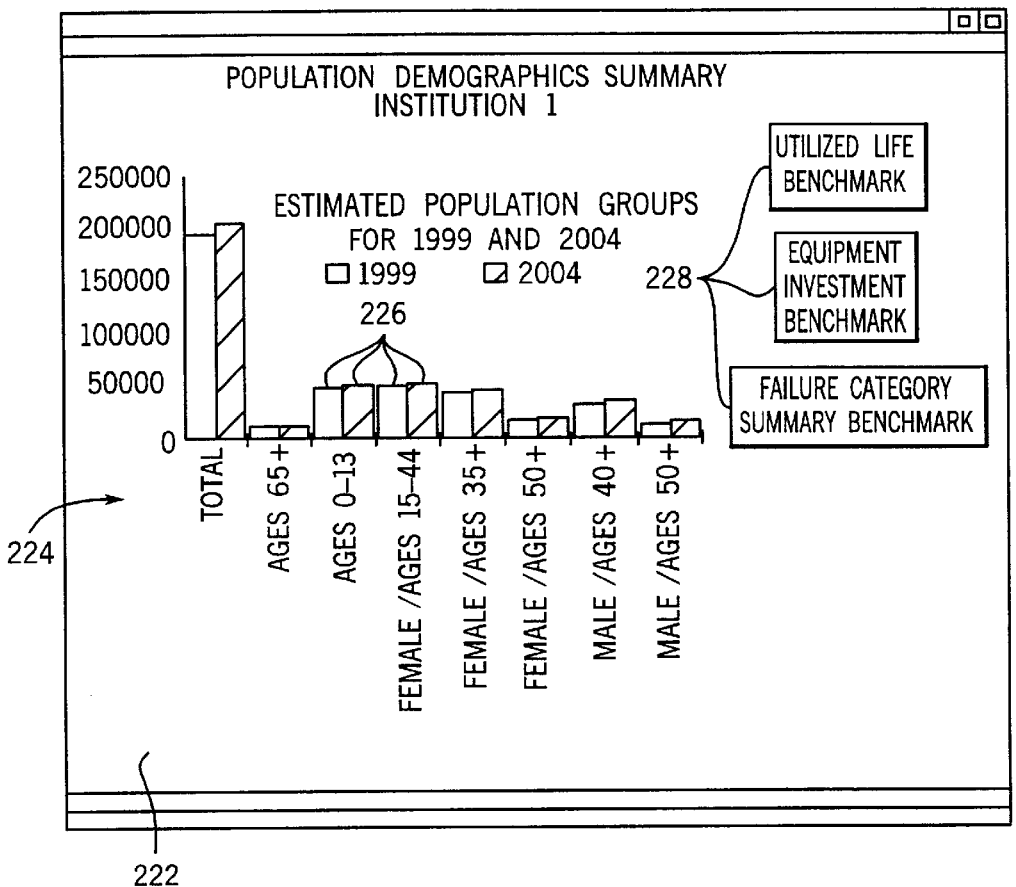

FIG. 12 illustrates an exemplary demographics summary page accessible through the executive summary tool 204 of FIG. 11. As noted above, the biomedical equipment data can be analyzed in accordance with demographic information for the institution so as to represent such factors as population groups within the institution (e.g., in-patients and out-patients), as well as the equipment utilized for patient care. In the summary page 222 of FIG. 12, a graphical summary display 224 provides an indication for the patient demographics of the subject institution. Also as noted above, where trending analysis is performed based upon current and historical collected data, trend graphics 226 may be provided. Also as noted above, where desired, equipment data collected for the institution, site, group, or department may be compared against profile data for known populations for similar institutions, and detailed benchmark reports comparing the subject institution to the selected profile may be accessed through virtual buttons 228. In the illustrated embodiment, such benchmarking is available through page 222 for comparing utilized life of equipment, investment, and failure records.

FIG. 13 illustrates a failure of benchmark summary table accessed through one of the virtual buttons 228 of FIG. 12. As illustrated in FIG. 13 the summary page 230 provides specific details for categories of equipment, as called out in a category column 232. When the collected equipment data is compared to similar data for a selected profile, the collected data may be classified in accordance with various classification ranges 234, to provide an indication of whether the subject institution's equipment performance falls within a statistical range of performance for the institution profile, or outside the range. Moreover, a summary may be provided as indicated at column 236 for equipment performance (e.g., failures) for equipment components covered by service arrangements. In the embodiment of FIG. 13, additional details are provided for the reference range in column 238 corresponding to ranges for the selected profile of the institution. Further comments and status data may be provided in additional column 240.

Figure 14:
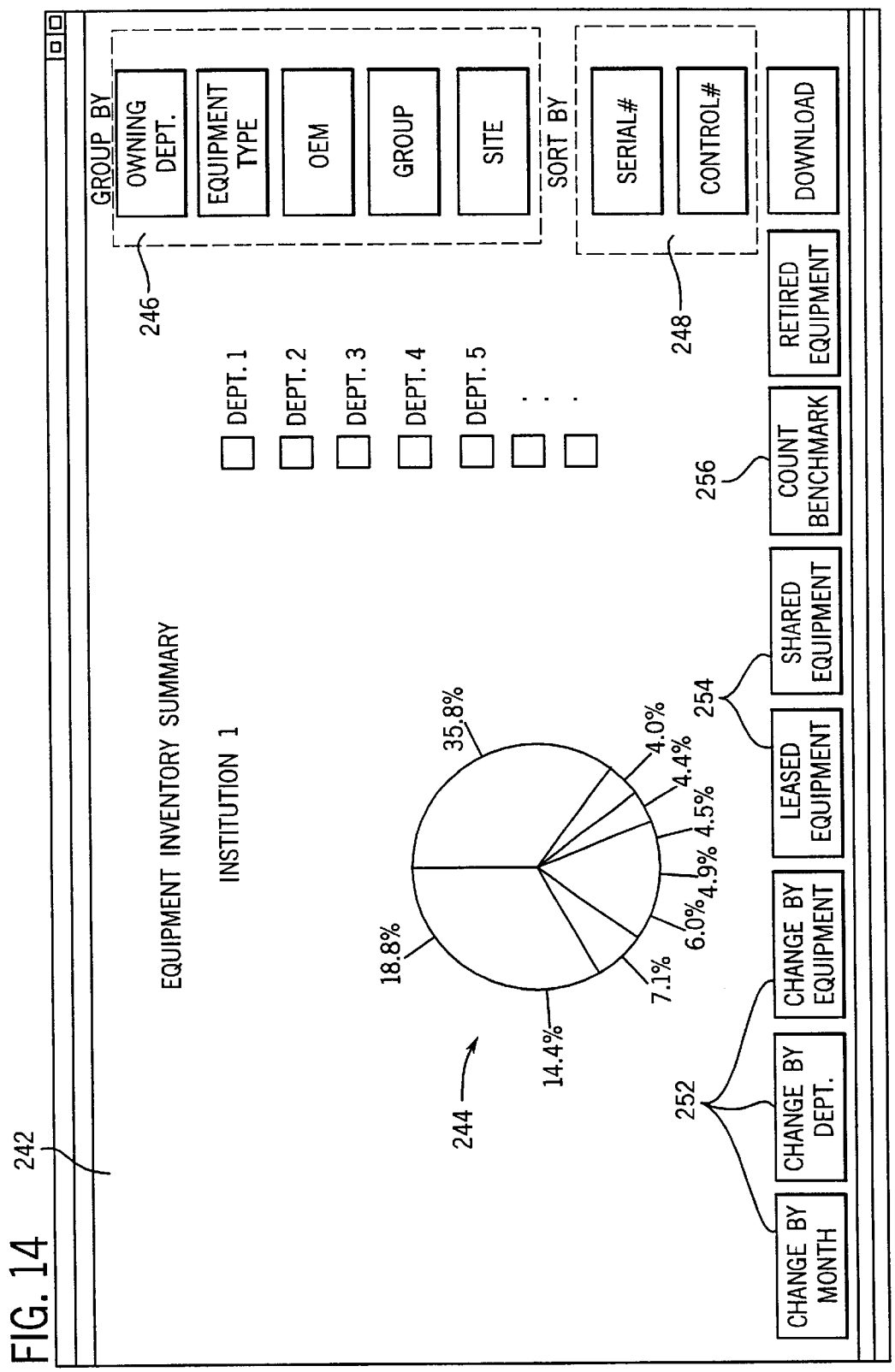

The biomedical equipment component data may also be summarized to analyze inventory on such bases as department, group, site, and so forth. FIG. 14 illustrates an inventory summary page by department as accessed through a virtual button 208 from the page illustrated in FIG. 11. As shown in FIG. 14, such inventory data may be summarized in a page 242, through the use of graphical techniques such as a graphical summary by department 244. The graphical techniques may present the data in any suitable fashion, such as through the pie chart illustrated in FIG. 14, through bar charts, line charts, or any other useful data presentation tools. In the embodiment illustrated in FIG. 14, the inventory summary page permits classification or sorting in accordance with a range of parameters stored for the equipment. By way of example, such classification may include the equipment type, the equipment manufacture, the group to which the institution or site locations belong, the site at which the equipment is located and so forth as indicated by the group tools 246. Additional sorting tools 248 may be provided, such as for viewing equipment details by serial number, control number, and so forth. As noted above, where equipment data is analyzed over a time range, such as by reference to historical equipment counts and performance, trending tools 252 may be provided, such as for viewing summary pages representing the changes by month, department, equipment, categories, and set forth. Moreover, depending upon the equipment title status, tools 254 may be provided for accessing pages presenting equipment inventory by title or ownership classifications. Finally, where benchmarking analysis is performed by reference to institution profiles and comparison to profiles for known institutions, benchmarking tools 256 may be provided for display of such comparisons.

Figure 15:
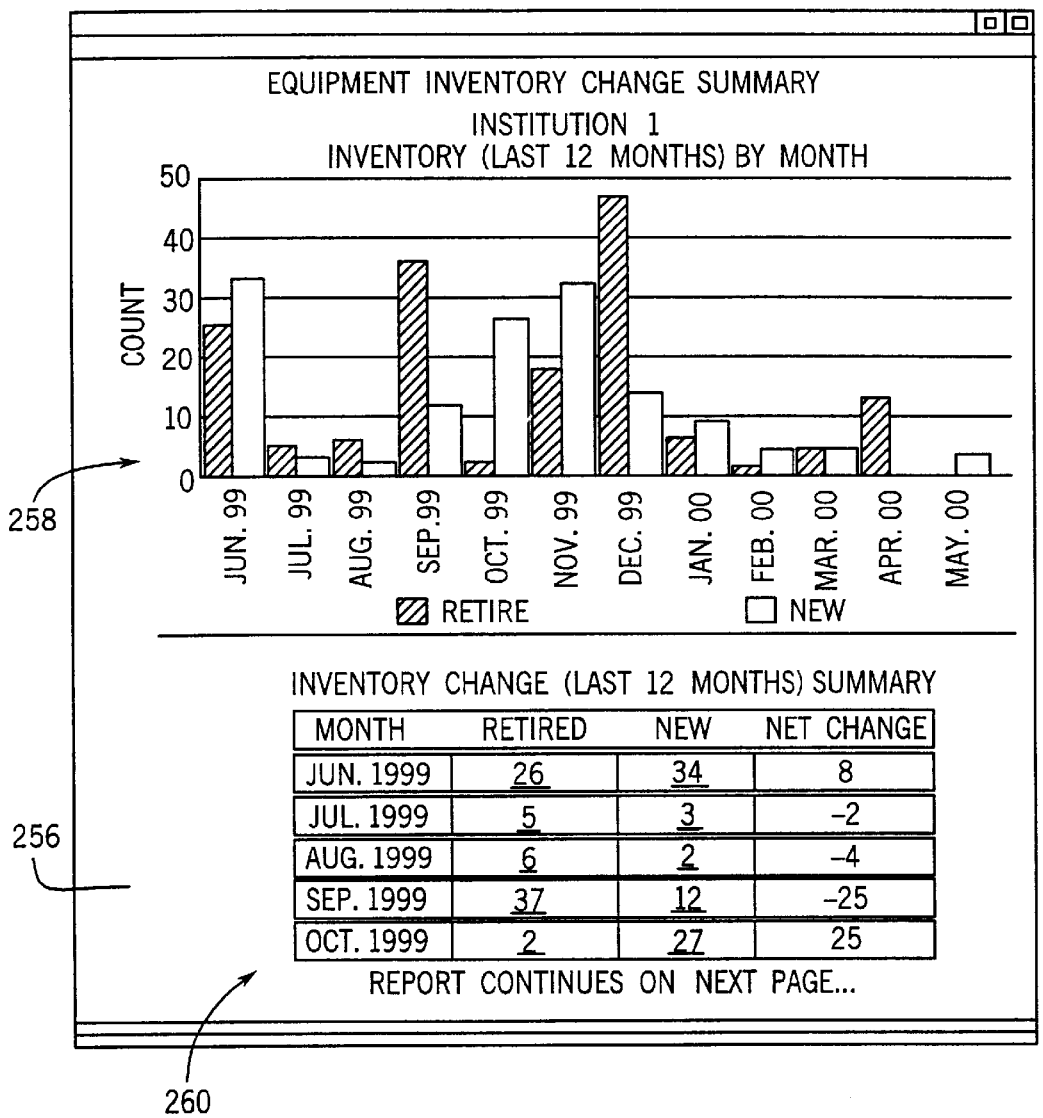
Figure 16:
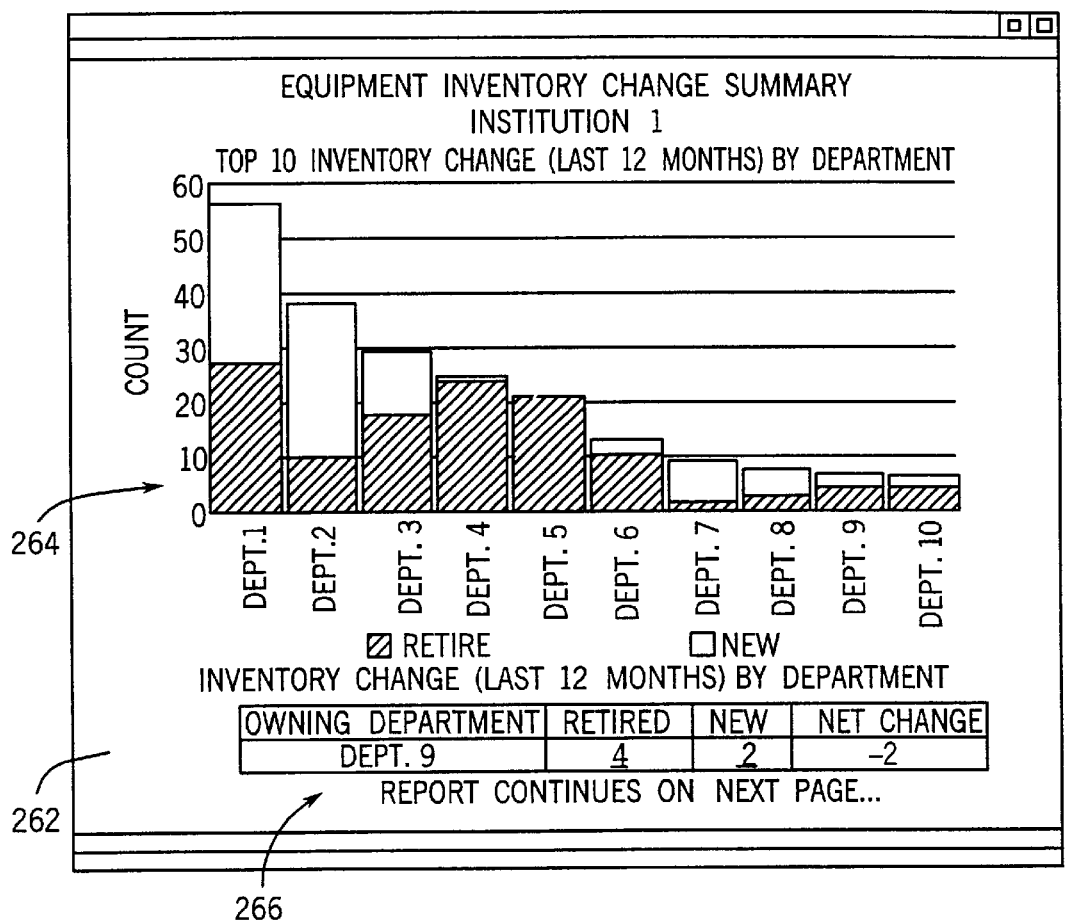

By way of example, FIG. 15 provides a page summarizing inventory trends or changes over a 12 months period, indicating both new equipment and retired equipment for an institution, as accessed via a virtual button 252 from FIG. 14. The inventory change summary page 256 provides a graphical summary 258 of the inventory changes. It should be noted that the graphical presentation may also present such changes by department, site, group, or any other desired functional portion of the institution. In the embodiment of FIG. 15, the information is also presented in a tabulated presentation indicating numerical counts for changes represented in the graphical presentation. Where desired, additional specific details may be offered through further pages, such as to provide an indication of the specific equipment or equipment types which have been retired or acquired. FIG. 16 illustrates an exemplary detailed summary page by department accessed through an additional virtual button 252 of FIG. 14. The departmental trend page 262 also provides a graphical indication 264 of the equipment changes per department, as well as a numerical count presentation 266 reflecting the changes.

As will be appreciated by those skilled in the art, the various presentations of inventory, inventory trends, inventory investment, and so forth, may be provided on various bases. For example, in the pages illustrated in FIGS. 14, 15 and 16, equipment counts are represented. However, by reference to the financial records for the institution or from a manufacturer, specific investment figures may be illustrated in a similar manner. Also, by reference to the financial records for individual components, and to regulations for taxing authorities (e.g., referenced by the group designations for the site locations) data presented in the reports may reflect book values for the equipment, depreciation to-date for the equipment, anticipated depreciation or book values, and so forth.

The comparison of the inventory data with similar data for institution profiles provides the opportunity to compare and benchmark the specific institution equipment performance. FIG. 17 illustrates an equipment count benchmark page accessed via a virtual tool 256 from the page of FIG. 14. When compared to the institution profile selected for the institution of interest, the benchmark information may compare such factors equipment counts, equipment investment, equipment performance, equipment failures, and so forth. Moreover, the information may be presented in accordance with various divisions or functional portions of the institution, such as departments, groups, sites, or as illustrated in FIG. 17 by sub-modalities. In the embodiment of FIG. 17, the benchmark presentation page 268 includes a category 270 for the equipment sub-modality, as well as a range classification column 272 indicating whether the basis for the comparison was within or outside a statistical range for the profile. An actual count column 274 is provided for each sub-modality, as well as a reference range column 276 for the specific profile selected. Other information, such as comments or status may be provided in a column 278. By way of example, in a present embodiment, where the profile population is insufficient to provide a reliable statistical basis for comparison (e.g., less than 20 institutions) a comment may be provided in column 278 indicating that this is the reason for a "no status" reference in the benchmark presentation.

Figure 18:
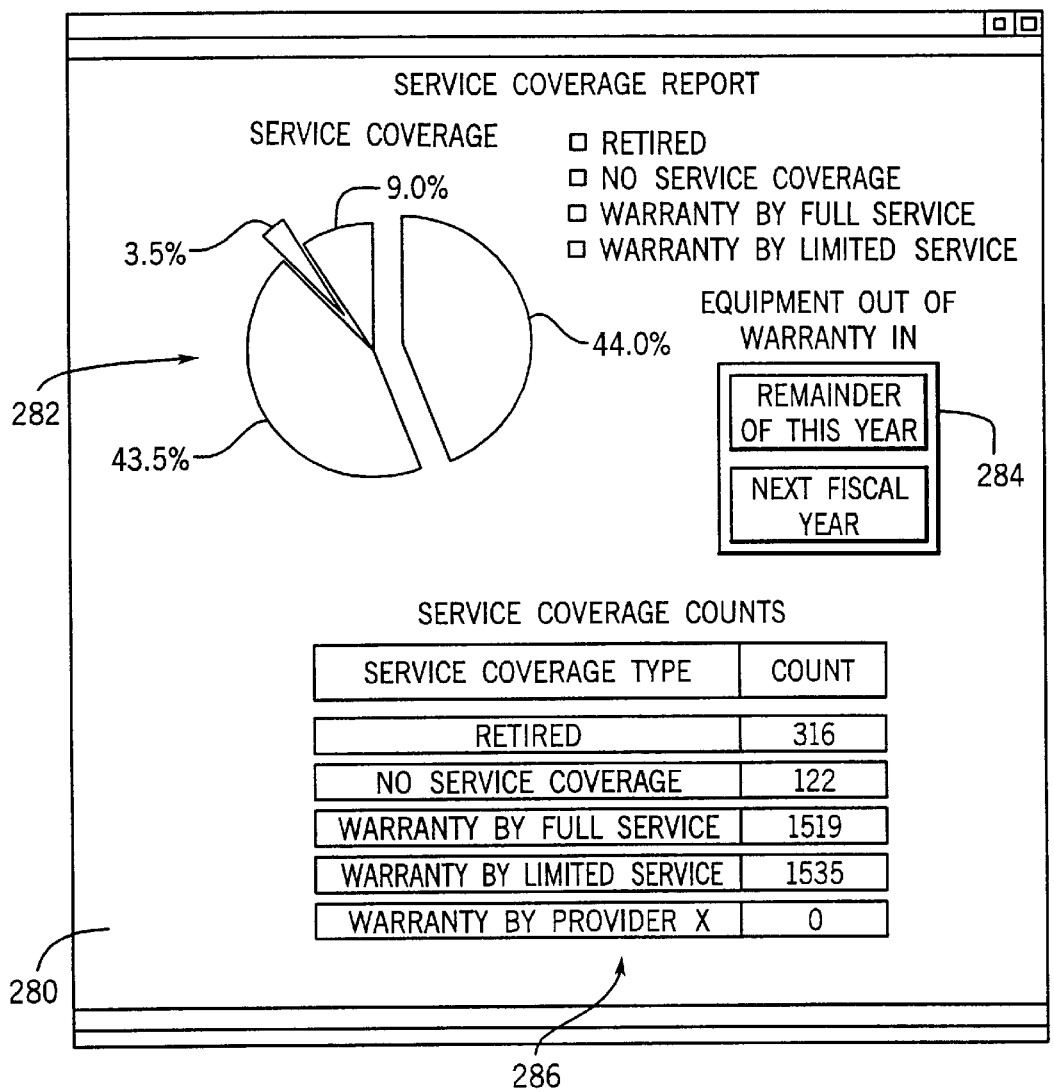

As described above, the present technique also provides an extremely useful tool for analyzing service coverage of biomedical equipment of the institution. FIG. 18 illustrates an exemplary report page summarizing service coverage for such equipment. The summary page 280 conveniently provides a graphical summary 282 for the level of service arrangement coverage or specific biomedical equipment. The page also provides tools 284 permitting the user to navigate to more detailed pages summarizing trends in service coverage, particularly service arrangements which will extend through a desired period and summaries of time periods during which service coverage will expire. Additional data presentations 286 may be provided for summarizing counts or quantities of various types of equipment which are covered by service arrangements.

FIG. 19 illustrates an exemplary detailed report of service arrangement coverage for biomedical equipment accessible from the summary page illustrated in FIG. 18. In the example FIG. 19, detailed information is provided in a summary page 288, and may be sorted in a variety of manners depending upon the analysis desired by the user. By way of example, designations or references may be provided by departments 290 to which the equipment is assigned, by site location 292 at which the equipment is located, or by group 294 to which the site belongs. The information may also be presented by equipment type 296, and equipment manufacturer 298. Where desired, more detailed reports for each of these classifications may accessible from the summary page. Additional details 298 may be provided, such as manual numbers, model numbers, and so forth. Where desired, acquisition dates for the equipment may be provided in column 300, particularly where such dates serve as the basis for warranty or other service coverage. Detailed identification numbers may be provided as indicated at reference numeral 302, specifically identifying pieces of equipment and reference codes used by the institution for designating the equipment. Moreover, where desired, specific identifications of service providers 304 and expiration and renewal dates 306 for service arrangements with the providers may be summarized. Such summaries thus provide decisionsmakers for the institution with powerful tools for grouping and analyzing service coverage arrangements for specific equipment, and for anticipating needed changes or renewals in such coverage.

Figure 20:
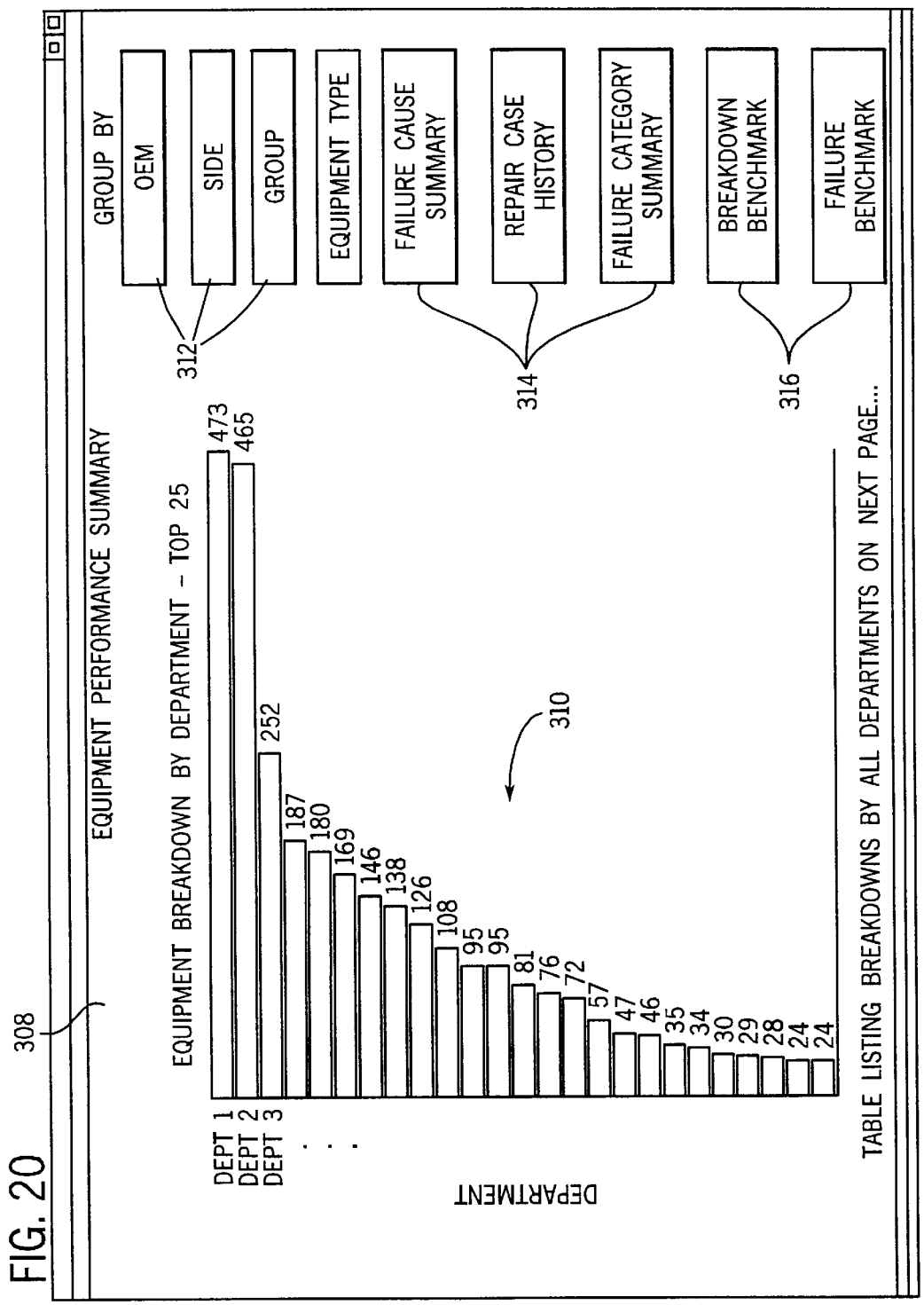

The equipment data stored in the centralized database for the institution may also be analyzed to identify parameters indicative of equipment performance. Such factors may include equipment utilization (e.g., number of days or cases for which the equipment was used) error codes, downtime, number of breakdowns, and so forth. An exemplary performance summary page 308 is illustrated in FIG. 20, accessible via a virtual button 212 from the main page of FIG. 11. In the exemplary embodiment of FIG. 20, the summary page provides a graphical summary 310 of specific equipment breakdowns by department. Similar presentations are available for other group designations, such as by equipment manufacturer, equipment site, site groups, and so forth, as indicated by the graphical buttons 312 in FIG. 20. Specific detailed analysis tools 314 may also be provided, such as for accessing virtual report pages summarizing causes of failure, repair histories, failure categories, and so forth. As noted above, the performance data may be compared against similar data for profiles of institutions derived from known populations of institutions, and benchmark pages may be presented through navigation tools 316, such as to provide breakdown benchmarking, failure benchmarking, and so forth.

By way of example, FIG. 21 illustrates a summary page for equipment performance (referenced by breakdowns) for a specific department of an institution. The departmental summary page 318, in the illustrated embodiment, provides references to the manufacturer of the equipment, as well as the equipment designation as indicated by reference numeral 320. Breakdown summary information 322 is provided, including a count of the breakdowns and a summariy of the performance over a desired analysis, such as a year. Specific identifications for the equipment are provided in columns 324, allowing for tracking of individual problematic equipment components, useful in analysis, replacement, and similar planning. Finally, additional details, such as time-in-service, and statistical information such as mean-time-to-repair, and mean-time-between-failures may be summarized as indicated at reference numeral 326. Further details may be accessible through detailed pages such as illustrated in FIG. 22. The detailed page 328 of FIG. 22 may present the performance information by functional portion of the institution, such as departments as illustrated at reference numeral 330, along with detailed analysis, such as a breakdown count as indicated at reference numeral 332.

Figure 23:
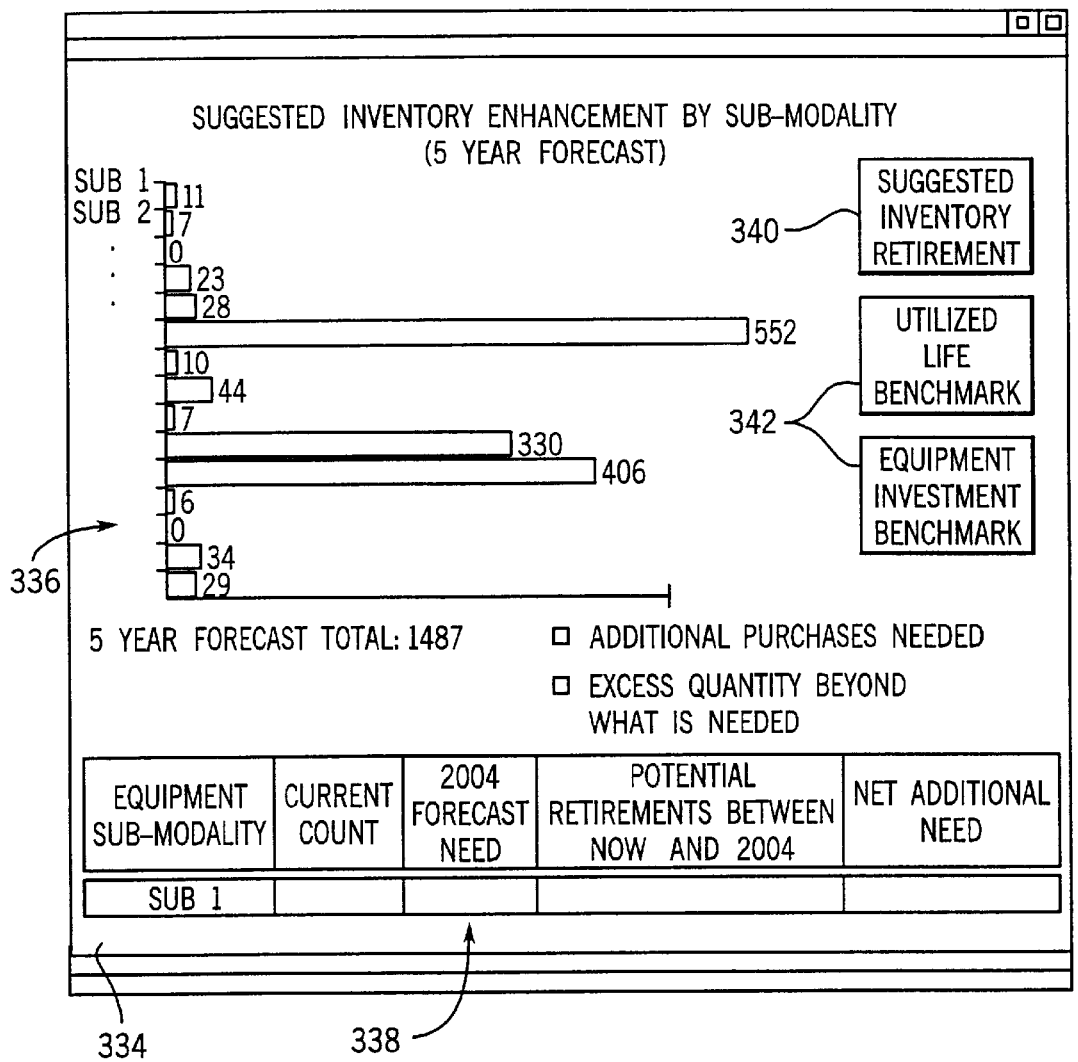

To aid in equipment management, forecasting, financial planning, and so forth, the present technique offers for data collection and reporting by analysis of potential needs for the institution, both in terms of newly acquired equipment, or retired equipment. Such forecasting tools may be based upon analysis of the equipment data stored in the centralized database, and upon factors such as the date at which the equipment entered into service, the anticipated life of the equipment, the depreciation period for the equipment, increases in anticipated demographics for the institution, and so forth. An exemplary forecast planning page 334 is illustrated in FIG. 23, accessed through a virtual button 214 from the main page at FIG. 11. As illustrated in FIG. 23, such pages may present forecasts by functional portion of the institution in graphical form 336. Such presentations may, as before, be subdivided by any suitable functional portion of the institution, such as departments, sites, groups, or as illustrated in FIG. 23, by sub-modality. The summary page may allow for additional navigation to suggested inventory changes, as indicated at reference numeral 340, as well as to benchmarking summaries for suggested equipment changes as indicated at reference numeral 342, providing comparisons of the suggested changes in the equipment inventory as compared to other institutions of similar profiles. Tabulated summaries of the data provided in the page may be summarized as indicated at reference numeral 338.

Additional, more detailed summaries accessible through the page illustrated in FIG. 23 are shown in FIGS. 24 and 25. As illustrated in these figures, a detailed planning page 344 may summarize specific changes suggested for the biomedical equipment, such as broken down by functional portion 346, in this case sub-modality. Current equipment counts (or equipment values) may be provided as indicated at reference numeral 348, as well as summaries of additions to, retirements from, and net changes in the inventory, as summarized at reference numeral 350. Even more detailed pages may be provided as shown in FIG. 25, such as through a long-term detailed forecast 352. A graphical summary 354 may be provided for the forecast, and a forecast may be subdivided by any suitable functional portion of the institution, sub-modality in the example of FIG. 25.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A computer-implemented method for managing and analyzing biomedical equipment data in a medical institution, the method comprising:

storing reference data in a reference database, the reference data including equipment utilization data, wherein the reference data includes data representative of equipment utilization by a known population of medical institutions;

operationally assigning a plurality of equipment components to at least two different functional portions of a medical institution of interest;

collecting data representative of identification, operation and operational assignment of the equipment components;

storing the collected data in a centralized database for the institution;

associating the collected data logically in the database for analysis of equipment inventory and for comparison to the reference data; and generating a profile for the medical institution of interest and comparing the reference data based upon the profile, wherein the profile is generated based at least upon size or demographics of the institution.

2. The method of claim 1, wherein the reference data includes historical data for the equipment inventory.

3. The method of claim 1, wherein the functional portions include different departments of the institution.

4. The method of claim 1, wherein the functional portions include geographically dispersed facility sites of the institution.

5. The method of claim 1, wherein the data is collected via a plurality of input stations.

6. The method of claim 1, wherein the data is collected via manual input and automatic acquisition from at least one of the equipment components.

7. The method of claim 1, further comprising generating a report of the equipment inventory.

8. The method of claim 7, wherein the report includes a comparison of the data for the institution of interest and the reference data.

9. The method of claim 7, wherein the reference database and the centralized database stored at different locations.

10. A computer-implemented method for analyzing biomedical equipment inventories in a medical institution, the method comprising:

storing reference equipment inventory data for a known population of medical institutions;

generating a plurality of reference institution profiles from the reference data;

collecting data representative of identification and operation of biomedical equipment components of an institution of interest;

storing the collected data in a centralized database for the institution;

generating an institution profile for the institution of interest, wherein the institution profile is based at least upon size or demographics of the institution; and comparing the collected data to the reference data based upon matching the institution profile with at least one of the reference profiles.

11. The method of claim 10, further comprising assigning the equipment components to functional portions of the institution, and wherein the collected data includes identification of the function portion to which the equipment components are assigned.

12. The method of claim 11, wherein the functional portions include different operational departments of the institution.

13. The method of claim 11, wherein the functional portions include geographically dispersed facility sites of the institution.

14. The method of claim 11, wherein the comparison includes comparison of equipment counts by functional portion.

15. The method of claim 10, wherein the data is collected via a plurality of input stations.

16. The method of claim 10, wherein the data is collected via manual input and automatic acquisition from at least one of the equipment components.

17. The method of claim 10, further comprising generating a report of the equipment inventory.

18. The method of claim 17, wherein the report includes a comparison of the data for the institution of interest and the reference data.

19. The method of claim 10, wherein the reference database and the centralized database stored at different locations.

20. A system for managing and analyzing biomedical equipment data in a medical institution, the system comprising:

a reference database including reference data representative of reference biomedical equipment utilization, wherein the reference database includes data compiled based upon equipment utilization by a known population of medical institutions;

a centralized institution equipment database including institution data representative of identification, operation and operational assignment of biomedical equipment components to at least two different functional portions of the medical institution; and a data analysis module configured to compare data from the reference database to data from the centralized database, wherein the data analysis module is configured to compare the data based upon a profile of the medical institution, wherein the profile is generated based at least upon size or demographics of institution.

21. The system of claim 20, wherein the reference database and the centralized database are stored at different locations.

22. The system of claim 20, comprising a plurality of data input stations for inputting the institution data into the centralized database.

23. The system of claim 20, wherein the centralized database is stored on at least two different memory devices.

24. The system of claim 20, wherein the medical institution includes a plurality of different departments and the function portions include the departments.

25. The system of claim 20, wherein the medical institution includes a plurality of geographically dispersed facility sites, and wherein the functional portions include the facility sites.

26. The system of claim 20, further comprising a report generation module configured to generate reports based upon the comparisons performed by the analysis module.

27. The system of claim 26, including a network interface for transmitting the report via a configurable network link.

28. The system of claim 27, wherein the configurable network link includes the Internet.

29. A system for managing and analyzing biomedical equipment data in a medical institution, the method comprising:

means for storing reference data in a reference database, the reference data including equipment utilization data, wherein the reference data includes data representative of equipment utilization by a known population of medical institutions;

means for operationally assigning a plurality of equipment components to at least two different functional portions of a medical institution of interest;

means for collecting data representative of identification, operation and operational assignment of the equipment components;

means for storing the collected data in a centralized database for the institution;

means for associating the collected data logically in the database for analysis of equipment inventory and for comparison to the reference data; and means for generating a profile for the medical institution of interest and comparing the reference data based upon the profile, wherein the data analysis module is configured to compare the data based upon a profile of the medical institution, wherein the profile is generated based at least upon size or demographics of institution.

* * * * *